US012661051B2

(12) United States Patent
Noffke et al.

(10) Patent No.: US 12,661,051 B2
(45) Date of Patent: Jun. 23, 2026

(54) ELECTROCARDIOGRAM INTERPRETATION

(71) Applicant: Welch Allyn, Inc., Skaneateles Falls, NY (US)

(72) Inventors: Patrick James Noffke, Hartland, WI (US); Nicoletta Marzocchi, Bologna (IT); Reyhaneh Sepehr, Fox Point, WI (US); Eugene G. Urrutia, Apex, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 240 days.

(21) Appl. No.: 18/468,434

(22) Filed: Sep. 15, 2023

(65) Prior Publication Data

US 2024/0099638 A1 Mar. 28, 2024

Related U.S. Application Data

(60) Provisional application No. 63/376,618, filed on Sep. 22, 2022.

(51) Int. Cl.
| | |
|---|---|
| *A61B 5/35* | (2021.01) |
| *A61B 5/00* | (2006.01) |
| *A61B 5/339* | (2021.01) |
| *A61B 5/367* | (2021.01) |

(52) U.S. Cl.
CPC ................ *A61B 5/35* (2021.01); *A61B 5/339* (2021.01); *A61B 5/367* (2021.01); *A61B 5/7267* (2013.01)

(58) Field of Classification Search
CPC ........... A61B 5/35; A61B 5/339; A61B 5/367; A61B 5/7267; A61B 5/355; A61B 5/358; A61B 5/36; A61B 5/364; A61B 5/742; A61B 5/0006; A61B 5/0205; A61B 5/021; A61B 5/369; A61B 5/4806; A61B 5/746; A61B 5/333; G16H 50/20
See application file for complete search history.

(56) References Cited

U.S. PATENT DOCUMENTS

| | | | |
|---|---|---|---|
| 9,408,550 B2 | 8/2016 | Stanczak et al. | |
| 10,631,750 B2 * | 4/2020 | Chen | A61B 5/364 |
| 11,013,470 B2 | 5/2021 | Shakur et al. | |
| 11,017,902 B2 * | 5/2021 | Sherkat | G06N 3/08 |

(Continued)

FOREIGN PATENT DOCUMENTS

| | | |
|---|---|---|
| CN | 111956208 A | 11/2020 |
| CN | 113598787 A | 11/2021 |

(Continued)

OTHER PUBLICATIONS

Wikipedia, Electrocardiogramassed Aug. 23, 2025, https://en.wikipedia.org/wiki/Electrocardiogramaar: 2025).*

(Continued)

*Primary Examiner* — Jonathan T Kuo
(74) *Attorney, Agent, or Firm* — Merchant & Gould P.C.

(57) ABSTRACT

A system for interpreting an electrocardiogram identifies a segment of the electrocardiogram having an abnormality using a machine learning algorithm. The system assigns an interpretation output to the segment of the electrocardiogram having the abnormality. The interpretation output describes a morphology of the abnormality.

17 Claims, 9 Drawing Sheets

(56) References Cited

U.S. PATENT DOCUMENTS

| | | | |
|---|---|---|---|
| 11,164,309 B2 | 11/2021 | Sati et al. | |
| 2015/0133805 A1* | 5/2015 | Stanczak | A61B 5/316 |
| | | | 600/300 |
| 2019/0029553 A1* | 1/2019 | Chen | A61B 5/339 |
| 2021/0125722 A1* | 4/2021 | Sherkat | G06V 10/764 |
| 2021/0383262 A1* | 12/2021 | Elen | G06F 18/2163 |
| 2022/0138511 A1 | 5/2022 | Xu et al. | |
| 2023/0397889 A1* | 12/2023 | Zhang | A61B 5/7267 |
| 2025/0082848 A1* | 3/2025 | Navara | A61B 5/4839 |

FOREIGN PATENT DOCUMENTS

| | | | |
|---|---|---|---|
| KR | 10-2322234 B1 | 11/2021 | |
| WO | 2022/011480 A1 | 1/2022 | |
| WO | 2022/087349 A1 | 4/2022 | |

OTHER PUBLICATIONS

Jones et al., "Improving ECG Classification Interpretability using Saliency Maps," 2020 IEEE 20th International Conference on Bioinformatics and Bioengineering (BIBE), pp. 675-682 pages (2020).

Saliency map, Wikipedia, https://en.wikipedia.org/wiki/Saliency_map, 6 pages (Aug. 18, 2022).

* cited by examiner

FIG. 3

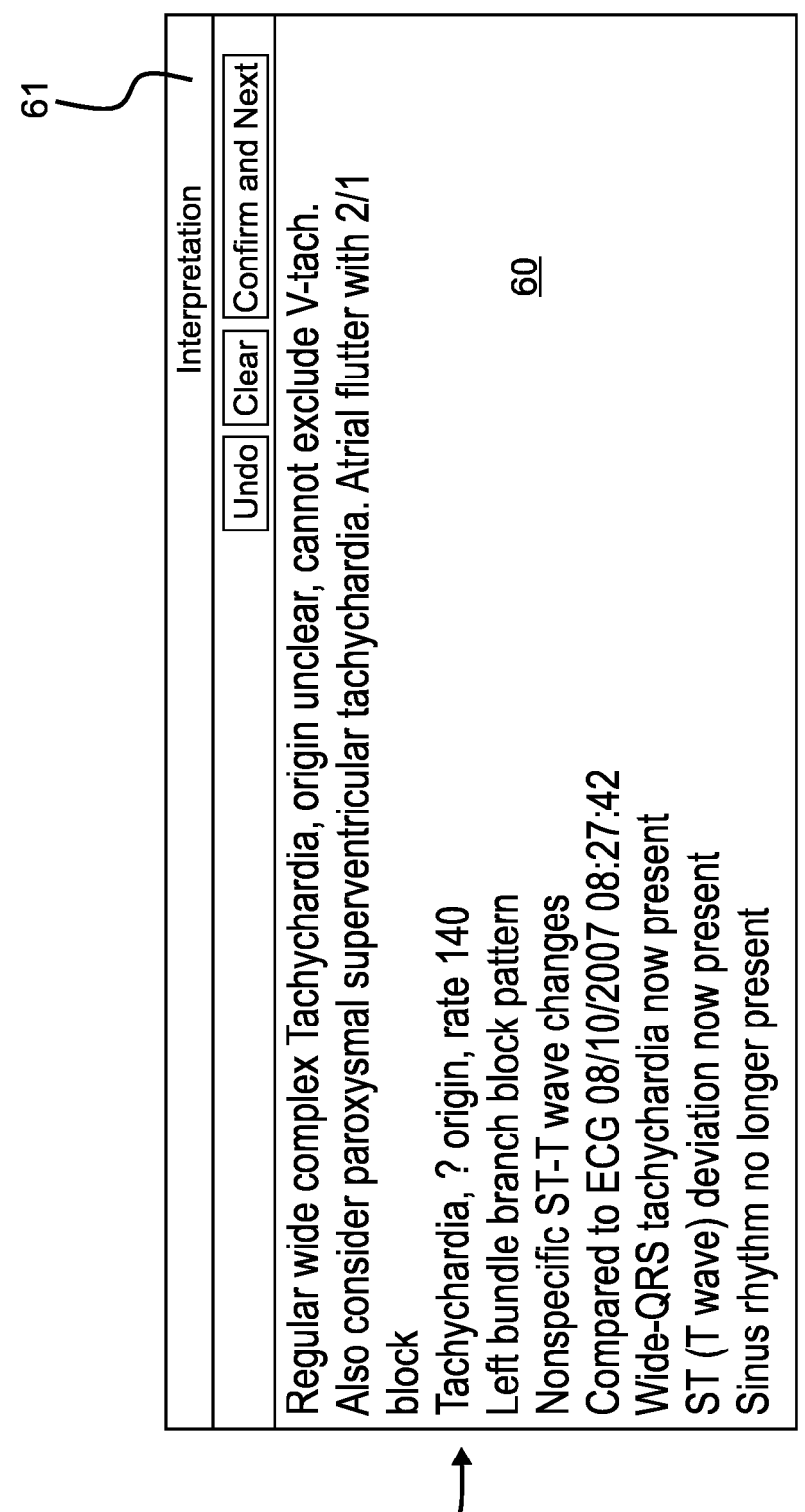

Interpretation

Undo | Clear | Confirm and Next

Regular wide complex Tachychardia, origin unclear, cannot exclude V-tach.
Also consider paroxysmal superventricular tachychardia. Atrial flutter with 2/1 block
Tachychardia, ? origin, rate 140
Left bundle branch block pattern
Nonspecific ST-T wave changes
Compared to ECG 08/10/2007 08:27:42
Wide-QRS tachychardia now present
ST (T wave) deviation now present
Sinus rhythm no longer present

60

61

65

61

Interpretation

Undo | Clear | Confirm and Next

Normal sinus rhythm, rate 82
Left bundle branch block
Low amplitude P waves.
Compared to ECG 08/11/2007 10:52:03
Wide-QRS tachycahrdia now present
ST (T wave) deviation now present

68

Electronically Signed On 08-17-11 17:43:09 EDT by Doctor Smith, MD

88

60

600

604

800

802
Identify Segment

804
Appy Transformations

806
Feed CNN

808
Determine Largest Return to Normal

810
Generate Interpretation Output

902

Sinus Rhythm ( ⟶ ) with occasional ventricular premature complexes ( ⟶ )
Right Bundle Branch Block ( ⟵----- )
Left Posterior Fascicular Block
Inferior myocardial infarction, possibly acute ( ⟵ )
*Acute MI*

ELECTROCARDIOGRAM INTERPRETATION

BACKGROUND

An electrocardiogram (ECG) is a common diagnostic tool used to assess cardiac function. The ECG measures electrical activity of the heart from electrodes positioned at different points on a patient's body. Key features of the ECG include the P-wave, QRS complex, and T-wave, each representing a different stage of the heartbeat. These features are often analyzed for detection of abnormalities affecting the rhythm and electrical activity of the heart.

SUMMARY

In general terms, the present disclosure relates to electrocardiogram interpretation. In one possible configuration, an interpretation output is assigned to describe a morphology of an abnormality detected by a machine learning algorithm. Various aspects are described in this disclosure, which include, but are not limited to, the following aspects.

One aspect relates to a system for interpreting an electrocardiogram, the system comprising: at least one processing device; and a memory device storing instructions which, when executed by the at least one processing device, cause the at least one processing device to: receive the electrocardiogram; identify a segment of the electrocardiogram having an abnormality using a machine learning algorithm; and assign an interpretation output to the segment of the electrocardiogram having the abnormality, the interpretation output describing a morphology of the abnormality.

Another aspect relates to a system for generating an electrocardiogram, the system including: one or more electrodes for receiving heart electrical signals; at least one processing device connected to the cardiograph device; and a memory device storing instructions which, when executed by the at least one processing device, cause the at least one processing device to: generate an electrocardiogram based on the heart electrical signals; display the electrocardiogram on a display device; identify a segment of the electrocardiogram having an abnormality using a machine learning algorithm; and assign an interpretation output to the segment of the electrocardiogram having the abnormality, the interpretation output describing a morphology of the abnormality.

Another aspect relates to a method of interpreting an electrocardiogram, the method comprising: generating an electrocardiogram based on heart electrical signals; displaying the electrocardiogram; identifying a segment of the electrocardiogram having an abnormality using a machine learning algorithm; and assigning an interpretation output to the segment of the electrocardiogram having the abnormality, the interpretation output describing a morphology of the abnormality.

DESCRIPTION OF THE FIGURES

The following drawing figures, which form a part of this application, are illustrative of the described technology and are not meant to limit the scope of the disclosure in any manner.

FIG. 3 illustrate an example of an interpretation box that includes interpretive statements displayed in the graphical user interface of FIG. 2.

DETAILED DESCRIPTION

ECG acquisition devices often provide, together with graphic ECG waveforms, automatic measurements (e.g., heart rate) and a suggested textual description of the ECG findings, known as an interpretive algorithm. Currently, interpretive algorithms do not replace physician reading. Therefore, an over-reading process is often needed, introducing a delay of confirmed interpretation of 24-48 hours for the routine workflow, or requires ad-hoc consultation of a specialist in emergency care. In some instances, interpretive algorithms are erroneous causing inappropriate treatment (e.g., inappropriate prescription of anticoagulants with incorrect atrial fibrillation interpretation), inappropriate tests (e.g., inappropriate catheterization lab testing with incorrect acute myocardial infarction (AMI) interpretation), and interruptions in care.

Machine learning provides an opportunity to improve the accuracy and speed of ECG analysis. However, machine learning algorithms are typically black box models that are not interpretable by humans. Thus, clinicians are typically unable to understand and verify how interpretations and/or determinations are made by machine learning algorithms.

Figure 1:
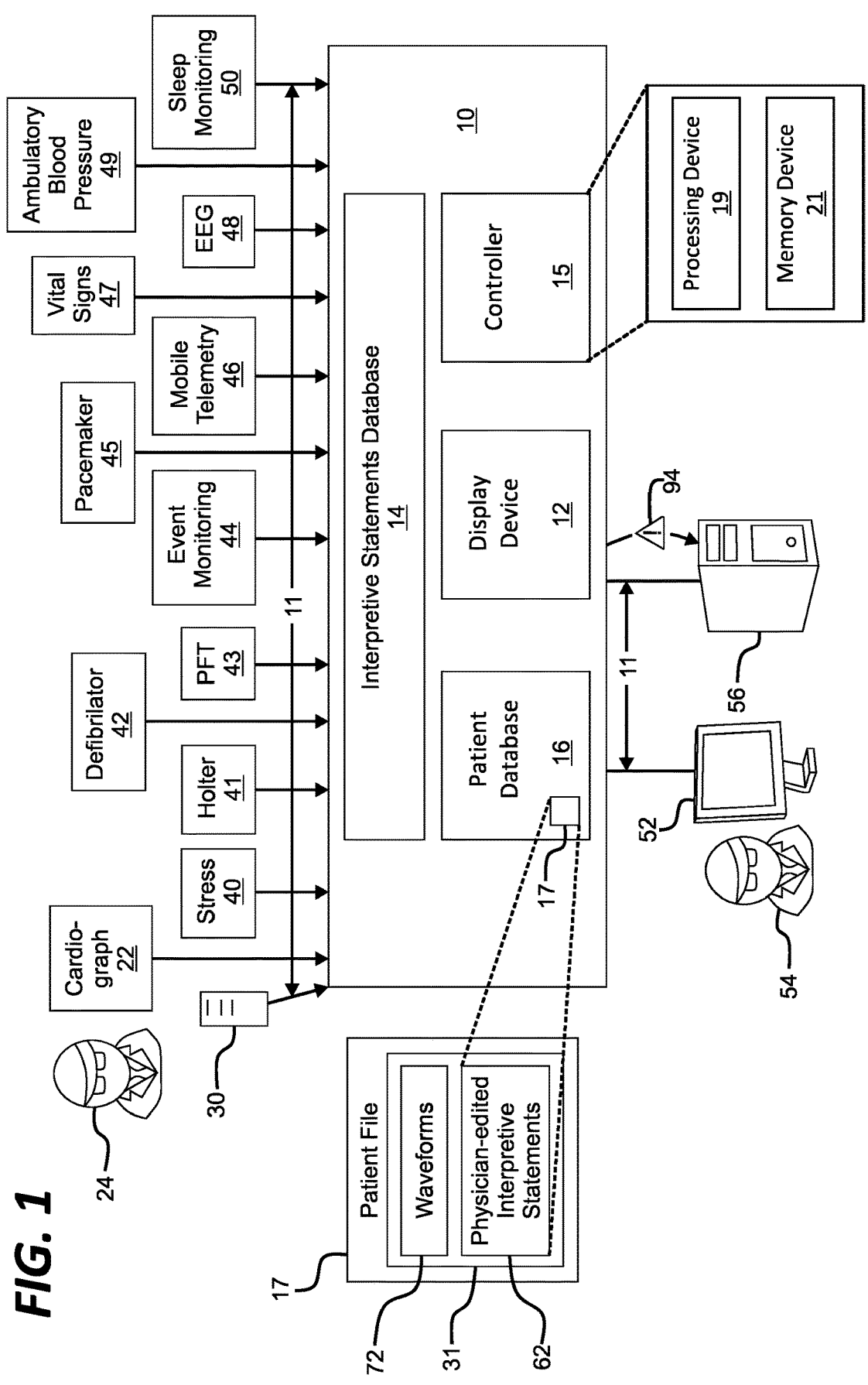
FIG. 1 schematically illustrates an example of a system for interpreting an electrocardiogram.

FIG. 1 schematically illustrates an example of a system 10 for analyzing and interpreting an electrocardiogram (ECG) of a patient 24. The system 10 allows a clinician 54 to view and edit one or more clinical reports 30 that include ECG recordings from the patient 24, and to trigger one or more critical alerts 94. In some instances, the system 10 includes aspects of the system described in U.S. Pat. No. 9,408,550 B2, entitled EVOLVING SERIAL COMPARISON SYSTEM WITH CRITICAL ALERT NOTIFICATIONS, issued on Aug. 9, 2016, the disclosure of which is hereby incorporated by reference in its entirety.

As shown in FIG. 1, a cardiograph 22 generates the clinical reports 30 that include the ECG recordings of the patient 24. In some examples, the cardiograph 22 can include one or more leads that attach to a chest of the patient 24 for measuring the ECG recordings. The system 10 receives the clinical report 30 from the cardiograph 22 via a connection such as through Wi-Fi, a local area network (LAN), the Internet, or other network, via a network interface 11.

Figure 2:
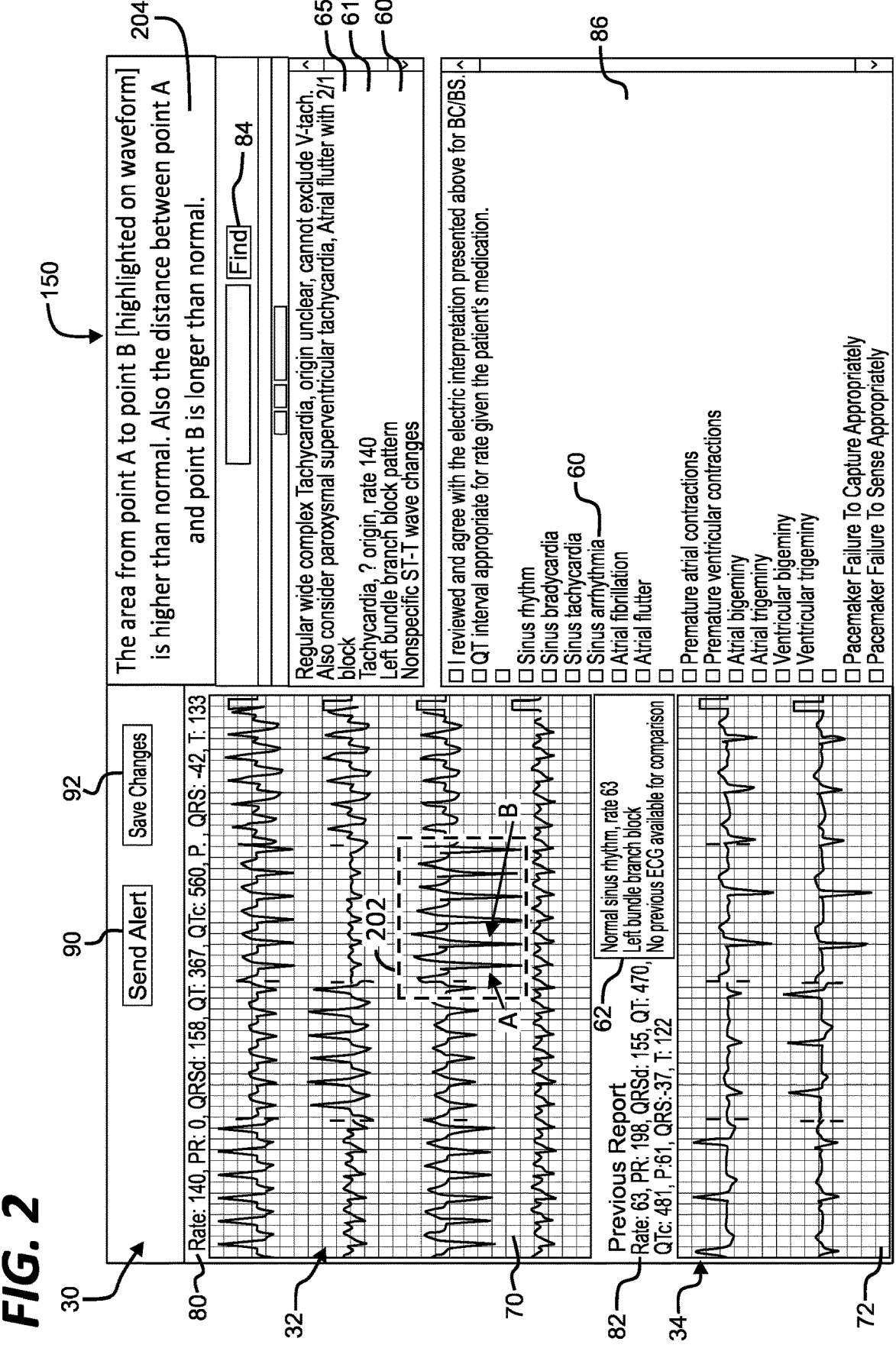
FIG. 2 is an example of a graphical user interface generated by the system of FIG. 1.

FIG. 2 illustrates an example of a graphical user interface (GUI) 150 generated by the system 10 for viewing and editing the clinical reports 30. The clinical report 30 displayed on the GUI 150 includes an electrocardiogram waveform 70 and physiological measurements 80 such as heart rate, pulse rate, blood oxygen saturation (SpO2), ECG QRS duration (QRSd), QT interval, and the like. In some instances, the GUI 150 is displayed on a workstation 52 used by the clinician 54. In further instances, the GUI 150 is displayed on the cardiograph 22. In yet further instances, the GUI 150 is displayed on a display device 12 of the system 10.

In this example, the clinical report 30 includes interpretive statements 60 generated from an algorithm that analyzes the electrocardiogram waveform 70 and the physiological measurements 80. The interpretive statements 60 include diagnostic classifications of the state and behavior of the heart as determined from the electrocardiogram waveform 70. The diagnostic classifications can be stored in an interpretive statements database 14 of the system 10. The algorithm is a machine learning algorithm that advances an ECG overread process by introducing artificial intelligence into interpretive algorithms to complement clinical workflows.

Upon receiving the clinical report 30, the system 10 may access a patient file 17 and retrieve a previous clinical report 34 for the patient 24. The previous clinical report 34 may include a previous electrocardiogram waveform 72 and previously edited interpretive statements 62. As shown in FIG. 1, the system 10 can include a patient database 16 that stores the patient file 17. The system 10 can also communicate with a hospital patient records management system 56 to access the patient file 17, when the patient file 17 is stored in a separate system. The system 10 can also store a new clinical report 32 that includes the electrocardiogram waveform 70 and the physiological measurements 80 in the patient file 17.

The GUI 150 allows the clinician to view the new clinical report 32 and the previous clinical report 34 side-by-side, and to edit the interpretive statements 60. The GUI 150 displays the previous electrocardiogram waveform 72, previous physiological measurements 82, and previously edited interpretive statements 62 from the previous clinical report 34. The GUI 150 displays the new clinical report 32, which includes the electrocardiogram waveform 70, the physiological measurements 80, and the interpretive statements 60 displayed in an interpretation box 61. The clinician 54 can correct the interpretive statements 60 in the interpretation box 61 and resulting edited interpretive statements 68 (shown in FIG. 4).

The previously edited interpretive statements 62 include stored edits by the clinician 54 (or a different clinician) to the previous clinical report 34. The system 10 maps the previously edited interpretive statements 62 into one or more diagnostic codes of a structured data format to put the previously edited interpretive statements 62 into a format usable with a serial comparison algorithm. Each diagnostic code may uniquely identify a medical state. When no previous clinical report 34 is found, the system 10 can insert the statement "No previous report is available for comparison" into the interpretive statements 60.

Figure 4:
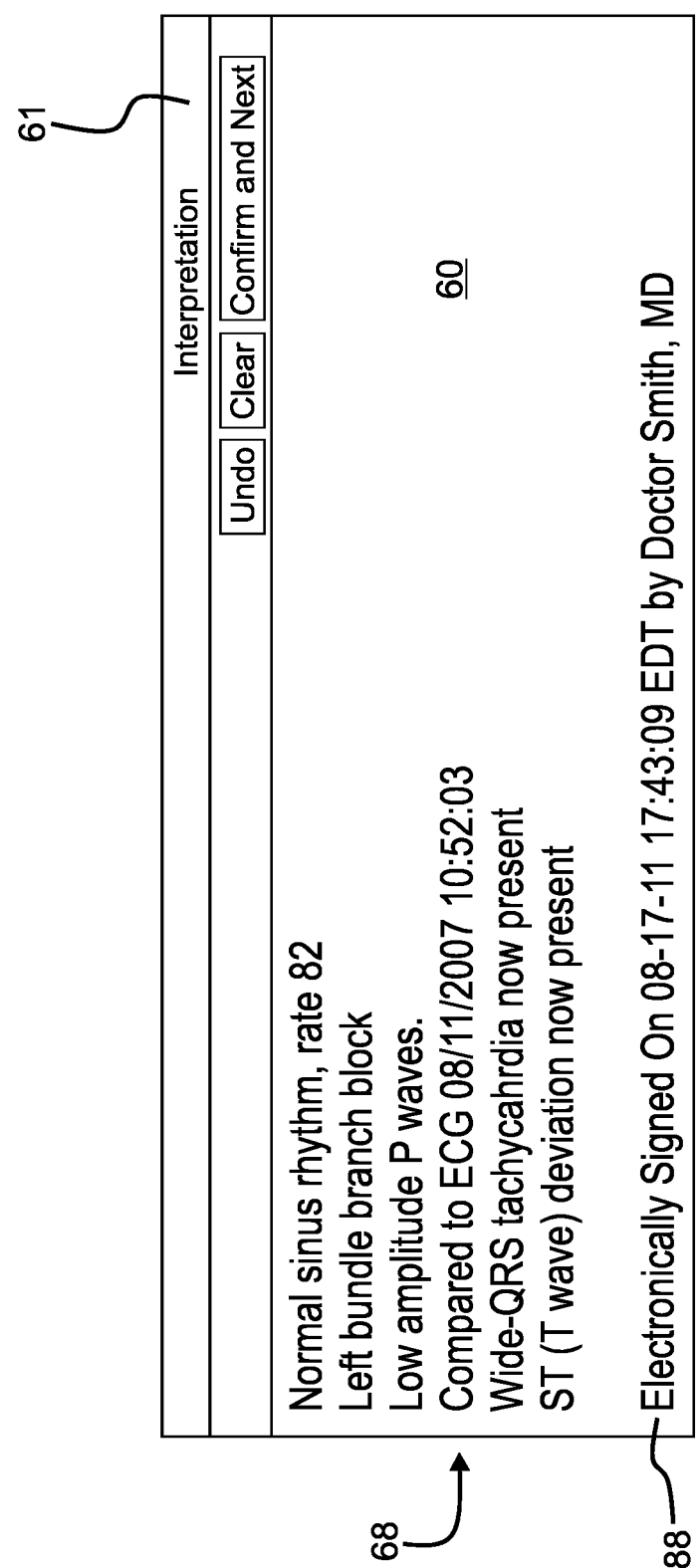
FIG. 4 illustrate another example of the interpretation box of FIG. 3 that includes edited interpretive statements.

FIGS. 3 and 4 illustrate examples of the interpretive statements 60. FIG. 3 illustrates the interpretation box 61 upon opening the new clinical report 32. The interpretive statements 60 are pre-populated into the interpretation box 61. The interpretation box 61 may be a free form text input box to permit the clinician 54 to edit the interpretive statements 60, delete one or more interpretive statements 60, and add interpretive statements 60.

FIG. 4 illustrates the interpretation box 61 after the clinician 54 has edited the interpretive statements 60 to create an updated interpretation of the physiological data that includes edited interpretive statements 68. The clinician 54 may create an electronic signature 88 to sign the edited interpretive statements 68.

The system 10 may perform an automated serial comparison of the previous clinical report 34 and the new clinical report 32 to generate comparison interpretive statements 65. The automated serial comparison includes determining diagnostic codes of the interpretive statements 60 from both the previous clinical report 34 and the new clinical report 32, and comparing the diagnostic codes to determine whether waveform changes have occurred.

When the new clinical report 32 includes an interpretive statement 60 corresponding to a diagnostic code that is not present in the previous clinical report 34, a modifier "now present" may be added to the interpretive statement 60 to generate the comparison interpretive statement 65. When the previous clinical report 34 includes an interpretive statement 60 and there is no interpretive statement 60 in that category in the new clinical report 32, a modifier "no longer present" is added to the interpretive statement 60 to generate the comparison interpretive statement 65. Otherwise, when no significant waveform changes are detected for a diagnostic code, the system 10 adds a modifier "remains" to the interpretive statement 60 to generate the comparison interpretive statement 65. Also, when additional waveform changes are detected, a "more prominent" or "less prominent" modifier may be added. Additionally, interpretive statements 60 may be added to the comparison interpretive statements 65 to consider rhythm changes, secondary rhythm changes, heart rate changes, and the like.

A search box 84 is provided allowing the clinician 54 to search for interpretive statements 60. When the search box is active, as each character of a search string is entered, the system 10 limits the interpretive statements 60 in the library box to those interpretive statements 60 matching the search string as entered at that point in time. This may permit the clinician 54 to select the interpretive statements 60 from a results list 86 without having to input a full matching search string. A categories dialog box (e.g., "Favorites") may be provided to permit the clinician 54 to limit the results list 86 to particular categories of interpretive statements 60.

The clinician 54 may input free-form text input into the interpretation box 61, or edit the text of the comparison interpretive statements 65 already present to generate edited interpretive statements 68. In some embodiments, the clinician 54 may be permitted to input free-form text using speech recognition. In other embodiments, the clinician 54 may be permitted to input free-form text using handwriting recognition. After editing, the clinician 54 may confirm the updates to the new clinical report 32 by clicking a save changes button 92.

The physician edited interpretive statements may be parsed to extract interpretive statements 60. Parsing may require the system 10 to first convert the physician edited interpretive statements into text form. For example, the system 10 may convert audio recordings of verbal physician edited interpretive statements to text. Similarly, the system 10 may convert handwriting to text. After physician edited interpretive statements are converted to text, spelling correction, grammatical correction and normalization, removal of punctuation, and the like may then normalize the resulting text. Interpretive statements 60 may then be parsed by splitting the physician edited interpretive statements into two or more sub-strings.

The system 10 classifies substrings to correspond to at least one diagnostic code of a structured data format. Classification can be accomplished by performing a lookup in the interpretive statements database 14 that includes spelling, abbreviations, and acronym variations of the interpretive statements 60. The system 10 can lookup the diagnostic code associated with the interpretive statement 60 and store the diagnostic code in the new clinical report 32 or use it to perform serial comparison to generate the comparison interpretive statements 65.

After editing, the clinician 54 confirms the updates to the new clinical report 32 by clicking a save changes button 92. After a clinician 54 has saved changes to the new clinical report 32, the system 10 checks the edited interpretive statements 68 for statements that require a critical alert 94 to be issued. If the edited interpretive statements 68 requires a critical alert 94, system 10 may remind the physician to issue a critical alert 94.

Similarly, a send alert button 90 may be provided to permit the clinician 54 to manually issue a critical alert 94. When a critical alert 94 is issued, the system 10 may then log the critical alert 94. The critical alert 94 may be logged in the patient database 16 of the system 10 or the hospital patient records management system 56. Alternatively, failure to issue a critical alert 94 may be logged to record that the critical alert 94 was affirmatively not issued.

Referring back to FIG. 1, the system 10 may receive additional physiological data in the clinical report 30, such as data collected from stress tests 40, a Holter monitoring 41, defibrillators 42, pulmonary function testing (PFT) 43, event monitoring 44, pacemaker 45, mobile telemetry 46, vital signs 47, EEG 48, blood pressure data 49, sleep monitoring 50, and the like. The clinical report 30 may be received from one or more connected devices such as medical devices, and may include interpretive statements 60 that are computer generated.

Aspects described herein are controlled by one or more controllers 15. The one or more controllers 15 may be adapted run a variety of application programs, access and store data, including accessing and storing data in associated databases, and enable one or more interactions via the user interface. The one or more controllers 15 include at least one processing device 19, and a memory device 21 storing instructions which, when executed by the at least one processing device, cause the at least one processing device to perform the functionalities described herein.

The at least one processing device 19 can include a central processing unit (CPU). The CPU can include a single microprocessor, or a plurality of microprocessors for configuring the CPU as a multi-processor system. The memory device 21 can include a main memory, such as a dynamic random access memory (DRAM) and cache, as well as a read only memory, such as a PROM, EPROM, FLASH-EPROM, or the like. The system 10 may also include any form of volatile or non-volatile memory. The main memory stores at least portions of instructions for execution by the CPU and data for processing in accordance with the executed instructions.

The one or more controllers 15 may also include one or more input/output interfaces for communications with one or more processing systems. Although not shown, one or more such interfaces may enable communications via a network, e.g., to enable sending and receiving instructions electronically. The communication links may be wired or wireless.

The one or more controllers 15 may further include input/output ports for interconnection with one or more output devices (e.g., display device 12, additional display devices including monitors and touchscreens, printers, and other output devices) and one or more input devices (e.g., keyboard, mouse, voice, touch, bioelectric devices, magnetic reader, RFID reader, barcode reader, touchscreen, motion-sensing input device, and other input devices) serving as one or more user interfaces for the controller 15. For example, the one or more controllers 15 may include a graphics subsystem to drive the output display. The links of the peripherals to the one or more controllers 15 may include wired and/or wireless connections.

Although summarized above as a PC-type implementation, those skilled in the art will recognize that the one or more controllers also encompasses systems such as host computers, servers, workstations, network terminals, and the like. Further one or more controllers may be embodied in a device, such as a mobile electronic device, like a smartphone or tablet computer. The term controller is intended to represent a broad category of components.

Hence aspects of the systems and methods provided herein encompass hardware and software for controlling the relevant functions. Software may take the form of code or executable instructions for causing a controller or other programmable equipment to perform relevant operations, where the code or instructions are carried by or otherwise embodied in a medium readable by the controller or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s) shown in the drawings. Volatile storage media include dynamic memory, such as main memory of such a computer platform. Common forms of computer-readable media therefore include for example: a floppy disk, a flexible disk, hard disk, magnetic tape, any other magnetic medium, a CD-ROM, DVD, any other optical medium, a RAM, a PROM and EPROM, a FLASH-EPROM, any other memory chip or cartridge, or any other medium from which a computer can read programming code and/or data. Many of these forms of computer readable media may be involved in carrying one or more sequences of one or more instructions to a processor for execution.

The algorithm performed on the electrocardiogram waveform 70 is a machine learning algorithm that can streamline clinician overread process and enhance patient outcomes by introducing artificial intelligence into interpretive algorithms, providing a more accurate, consistent, and reliable automatic interpretation of ECGs which elevates clinician confidence in identifying critical conditions, improving the recognition of artifact and prioritizing exams for review. For example, the algorithm can automatically learn to identify patterns in traditional and non-traditional ECG features, and that is capable of learning novel high level ECG patterns. The algorithm can include an ECG interpretation vocabulary that is better aligned with the current clinical uses of the ECG, may consider the reason the ECG was requested, its clinical and historical context, and its clinical actionability. In some examples, the algorithm is a deep learning algorithm. In some examples, the algorithm includes a convolutional neural network (CNN). In some further examples, the algorithm includes saliency mapping. In alternative examples, the algorithm includes activation mapping. In yet further example, the algorithm can include additional types of machine learning and artificial intelligence algorithms.

The algorithm is trained using a large number of historical digital ECGs together with objective evidence of "true" diagnosis and/or ECG interpretation. For example, depending on the prevalence of conditions and required accuracy, the algorithm can be developed using over a million historical digital ECGs. Evidence of a true diagnoses can include a signature of a human reader on a final ECG interpretation. However, it is known that human ECG readers can be biased by the original automatic interpretation, their own clinical experience, or simply make mistakes. Thus, multiple readings of the same ECG by more than one physician can be used for stronger evidence of true diagnosis. For some classes of ECG findings (e.g., those involving acute or historical myocardial infarctions) actual and/or historical clinical data can reinforce the evidence of true diagnosis. The larger and more variate the database of historical digital ECGs is, the more useful it is for the development (training) of the algorithm given presence of imperfect true diagnosis annotations. For the validation of accuracy claims and clinical acceptability, a smaller database with strong truth annotations can be used as well.

The historical digital ECGs are de-identified to remove protected health information for compliance with Health Insurance Portability and Accountability Act of 1996 (HIPAA) privacy rules. The database further includes one or preferably more automatic interpretations as well as human readings of the historical digital ECGs. Each interpretation category can include at least 100-1000 abnormal findings in various degrees (depending on the prevalence and clinical impact of the category), as well as at least 10 times as many normal findings. The human reading is performed by a group of physicians having clinical expertise of ECG interpretation, including but not limited to cardiologists and cardiac electrophysiologists.

As shown in FIG. 2, the algorithm generates an interpretation output 202 on the electrocardiogram waveform 70. The interpretation output 202 is assigned to a segment of the electrocardiogram waveform 70 where an abnormality is detected by the algorithm.

The interpretation output 202 is generated to describe a morphology of the abnormality to provide context enabling the clinician 54 to understand why the abnormality was detected by the algorithm. The interpretation output 202 provides a technical effect and/or a practical application in view of the black-box nature of machine learning algorithms, which make it difficult to understand how or why decisions are made. For example, the interpretation output 202 helps overcome challenges in using machine learning algorithms in healthcare applications, which the clinician 54 needs to be able to trust a model that can explain its decisions, especially when its decisions affect patient care and outcomes.

As an illustrative example, the GUI 150 includes a morphology statement box 204 to provide context to the abnormality detected by the algorithm in the interpretation output 202 of the electrocardiogram waveform 70. In the illustrative example provided in FIG. 2, morphology statement box 204 includes the statement "The area from point A to point B [highlighted on waveform] is higher than normal. Also, the distance between point A and point B is longer than normal." In another example, the system 10 displays the morphology statement box 204 inside the clinical report 30 where the electrocardiogram waveform 70 is displayed whenever the clinician 54 hovers their mouse cursor over the interpretation output 202.

The morphology statement box 204 differs from the interpretive statements 60 included in the clinical report 30 in that the interpretive statements 60 provide a pathology or diagnosis, whereas the morphology statement box 204 describes the morphology of the electrocardiogram waveform 70 including shapes and spatial features that cause the interpretive statements 60 to be generated by the algorithm. Thus, the morphology statement box 204 provides additional context when used together with the interpretive statements 60, and thus allows the clinician to understand the interpretive statements 60 outputted by the algorithm.

Figure 5:
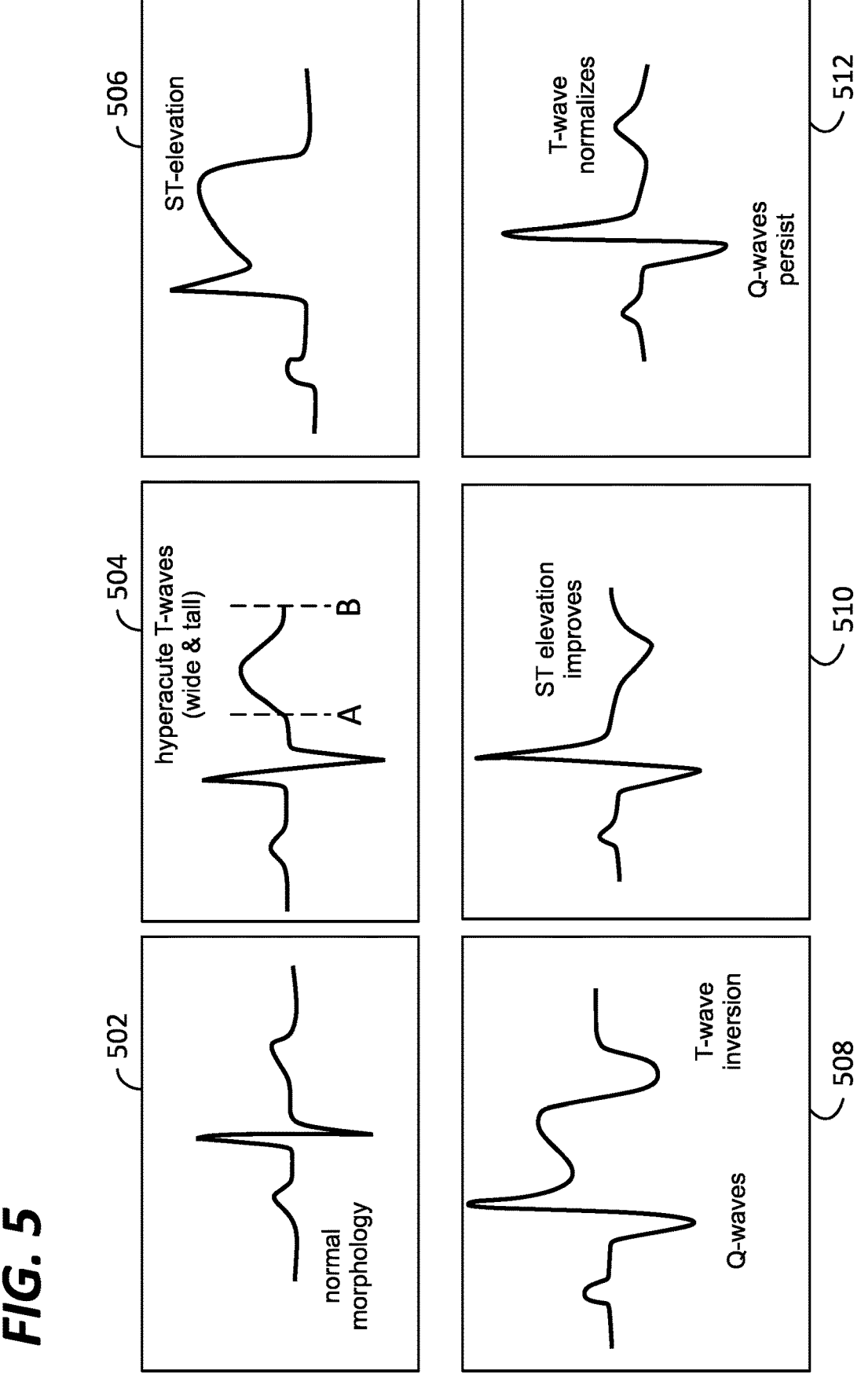
FIG. 5 illustrates examples of morphology markers displayed by the system of FIG. 1.

FIG. 5 illustrates examples of morphology markers 502-512 that the system 10 can display in addition to the morphology statement box 204, or as an alternative to the morphology statement box 204. The morphology markers 502-512 provide a visual reference for understanding why the abnormality is detected by the algorithm. In some examples, the system 10 displays the morphology markers 502-512 inside the clinical report 30 where the electrocardiogram waveform 70 is displayed whenever the clinician 54 hovers their mouse cursor over the interpretation output 202. In another example, the system 10 can display the morphology markers 502-512 inside the morphology statement box 204 to provide additional context. Additional locations for displaying the morphology markers 502-512 are possible.

In the example provided in FIG. 5, a first morphology marker 502 illustrates what a normal morphology should look like for the segment of the electrocardiogram waveform 70 where the abnormality is detected inside the interpretation output 202. In some examples, the system 10 displays the first morphology marker 502 as an overlay on top of the electrocardiogram waveform 70 such that the clinician 54 can visually see where the electrocardiogram waveform 70 deviates from the normal morphology. In another example, the system 10 displays the first morphology marker 502 next to the electrocardiogram waveform 70 allowing the clinician 54 to use the first morphology marker 502 as a visual reference for understanding why the abnormality is detected by the algorithm.

As further shown in FIG. 5, a second morphology marker 504 illustrates an example of an abnormal hyperacute T-wave pathology that is wide and tall compared to a baseline normal morphology shown in the first morphology marker 502. In some examples, the algorithm detects hyperacute T-waves by identifying this segment of the electrocardiogram waveform 70 as having the highest saliency (input to output gradient) in the T-wave area. A decrease in amplitude across the entirety of the electrocardiogram waveform 70 would lower a probability of the hyperacute T-wave interpretation. When used in combination with the morphology statement box 204, the algorithm can provide a meaningful statement "The area from point A to point B [as shown in the interpretation output 202 and/or second morphology marker 504] is higher than normal; the distance between point A and point B is longer than normal" to provide additional context.

As shown in FIG. 5, a third morphology marker 506 illustrates an example of an abnormal ST-elevation. A fourth morphology marker 508 illustrates an example of an abnormal Q-wave and T-wave inversion. A fifth morphology marker 510 illustrates an example of an abnormal Q-wave inversion, and improvement of the T-wave inversion. A sixth morphology marker 512 illustrates an example of an abnormal persistence of the Q-wave inversion, and normalization of the T-wave. The system 10 can display additional types of morphology markers such that the morphology markers 502-512 are provided by way of illustrative example.

Figure 6:
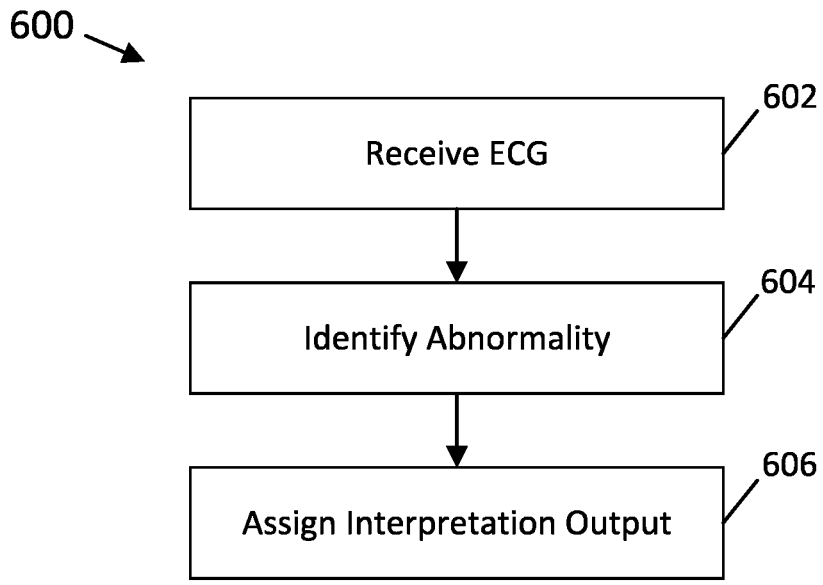
FIG. 6 schematically illustrates an example of a method of interpreting an electrocardiogram performed by the system of FIG. 1.

FIG. 6 schematically illustrates an example of a method 600 of interpreting an electrocardiogram. The method 600 can be performed by the system 10. The method 600 includes an operation 602 of receiving the electrocardiogram waveform 70. Operation 602 can include receiving the electrocardiogram waveform 70 from the cardiograph 22.

Next, the method 600 includes an operation 604 of identifying a segment of the electrocardiogram waveform 70 having an abnormality using a machine learning algorithm. The machine learning algorithm performed in operation 604 can include a deep learning algorithm. In some examples, the machine learning algorithm includes a convolutional neural network (CNN). In some examples, the machine learning algorithm includes saliency mapping. In alternative examples, the machine learning algorithm includes activation mapping.

Figure 7:
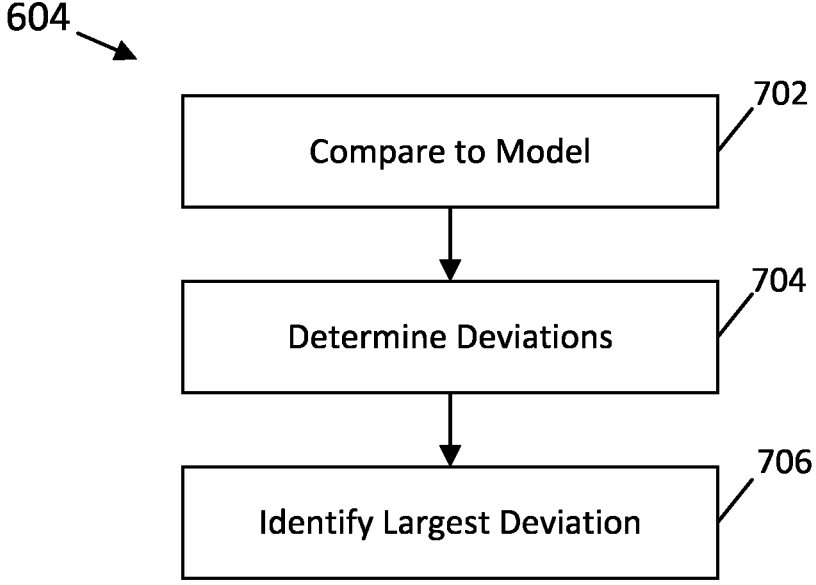
FIG. 7 schematically illustrates in more detail an example of an operation of identifying an abnormality using a machine learning algorithm in the method of FIG. 6.

FIG. 7 schematically illustrates in more detail an example of the operation 604 of identifying the segment of the electrocardiogram waveform 70 having the abnormality using the machine learning algorithm in the method 600. In this example, the operation 604 includes a step 702 of comparing the electrocardiogram waveform 70 to a normal electrocardiogram model. The normal electrocardiogram model is constructed and/or trained from a pool of ECG data. The ECG data is de-identified to remove protected health information for compliance with Health Insurance Portability and Accountability Act of 1996 (HIPAA) privacy rules. In some examples, the normal electrocardiogram model is a deep learning model. In further examples, the normal electrocardiogram model is a self-supervised model.

In the example of FIG. 7, the operation 604 next includes a step 704 of determining deviations from the normal electrocardiogram model based on the comparison in step 702. In step 706, the machine learning algorithm identifies features of the electrocardiogram waveform 70 that most sharply deviate from the normal electrocardiogram model for identifying the abnormality. Saliency mapping can be performed to identify the deviations from the normal electrocardiogram model by measuring the gradient of inputs and/or features to an outcome (e.g., abnormal interpretation for ECG). Areas of the electrocardiogram waveform 70 with the highest saliency correspond to the mostly sharply deviating features. In alternative examples, activation mapping can be performed to identify the deviations from the normal electrocardiogram model.

Referring back to FIG. 6, once the segment of the electrocardiogram waveform 70 having the abnormality is identified by using the machine learning algorithm in operation 604, the method 600 further includes an operation 606 of assigning an interpretation output 202 to the segment of the electrocardiogram waveform 70 having the abnormality. In accordance with the examples described above, the interpretation output 202 describes a morphology of the abnormality. For example, the interpretation output 202 can include a textual statement such as the morphology statement box 204 (shown in FIG. 2) that provides context to the abnormality detected by the machine learning algorithm. In addition, or as an alternative to the textual statement, the interpretation output 202 can include a morphology marker 502-512 that provides a visual reference for understanding why the abnormality is detected by the machine learning algorithm. Thus, advantages of the method 600 include, without limitation, improved understanding of abnormalities (e.g., interpretive statements 60) detected by a machine learning algorithm analysis of the electrocardiogram waveform 70.

Figure 8:
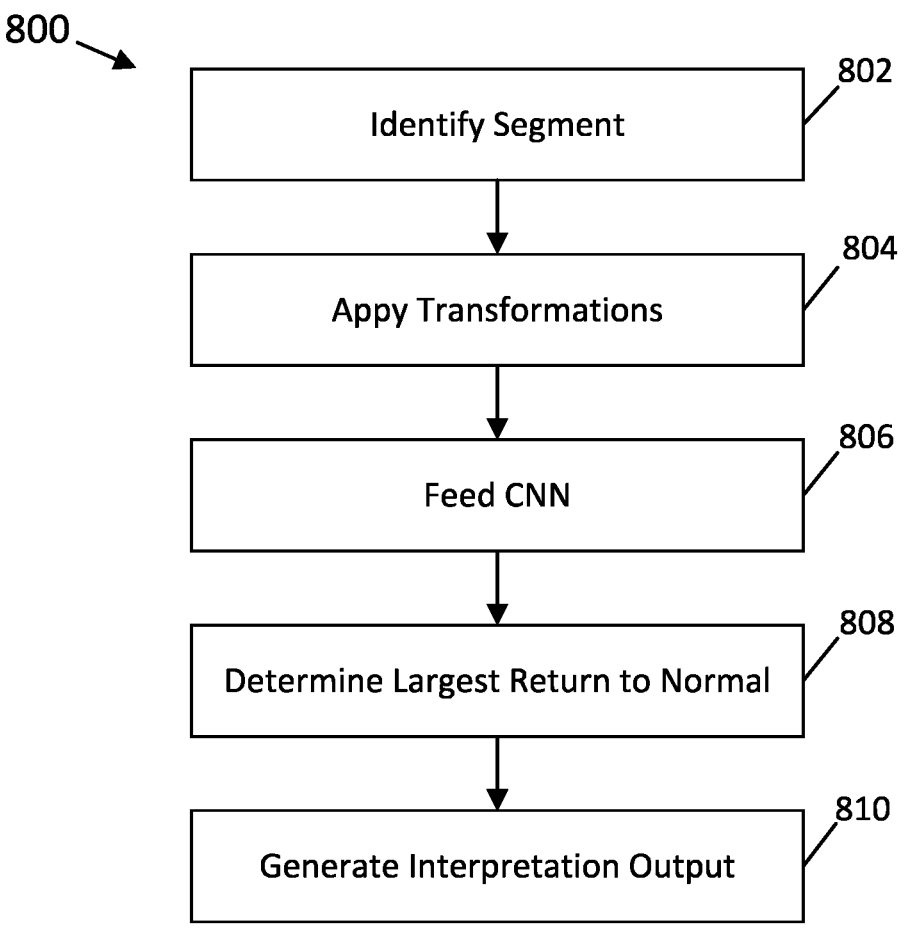
FIG. 8 schematically illustrates an example of a method of generating an interpretation output performed by the system of FIG. 1.

FIG. 8 schematically illustrates an example of a method 800 of generating an interpretation output 202. The method 800 can be performed by the system 10. The method 800 includes an operation 802 of identifying a segment within the electrocardiogram waveform 70 having a largest saliency. For example, the largest saliency is a largest gradient between the electrocardiogram waveform 70 and the normal electrocardiogram model. Operation 802 can include searching for established segment overlap with saliency. As an illustrative example, operation 802 can include identifying the segment having the largest saliency as any one of the P-wave, QRS complex, and T-wave portions in the electrocardiogram waveform 70.

Next, the method 800 includes an operation 804 of applying a range of transformations to the segment identified in operation 802. As an illustrative example, operation 804 can include applying about 20 to about 100 transformations to the segment.

Next, the method 800 includes an operation 806 of feeding the range of transformations through a convolutional neural network (CNN), and an operation 808 of determining which transformation produces the largest return to normal when fed back through the CNN. Return to normal means adjusting the morphology of the segment having the highest saliency to match or correspond to the normal electrocardiogram model.

Next, the method 800 includes an operation 810 of generating the interpretation output 202 as a reverse of the transformation that produces the largest return to normal. As an illustrative example, the interpretation output 202 generated by the method 800 can include "This wave appears elevated and elongated compared to baseline", which is indicative of a hyperacute T-wave abnormality. Hyperacute T-waves are wide and tall compared to baseline normal morphology of T-waves. The method 800 when performed by the system 10 can detect hyperacute T-waves as having the highest saliency (input to output gradient) in the T-wave portion of the electrocardiogram waveform 70. The method 800 can produce a meaningful statement for the clinician 54 to understand an interpretive statement 60 such as, for example, "The area from point A to point B [highlighted on the interpretation output 202] is higher than normal, and the distance between point A and point B is longer than normal."

Further illustrative examples of language that can be applied to the morphology statement box 204 by the method 800 to provide context about the abnormality detected by the machine learning algorithm can include, without limitation, detection of an abnormal amplitude of the electrocardiogram waveform (e.g., abnormal increase in the amplitude or abnormal decrease in the amplitude), detection of an abnormal length of a section/segment within the electrocardiogram waveform (e.g., an abnormal increase in length or an abnormal decrease in length), a detection of an abnormal slope of a section/segment within the electrocardiogram waveform (e.g., an abnormal increase in slope or an abnormal decrease in slope), and abnormal shape (e.g., second derivative, convex, concave, etc.). In some examples, the system 10 can further insert a segment into the electrocardiogram waveform 70 or delete a segment from the electrocardiogram waveform 70 as part of the interpretation output 202.

Additionally, the machine learning algorithms performed by the system 10 can look beyond traditional segments/ portions of the electrocardiogram waveform 70 (e.g., P-wave, QRS complex, and T-wave) for detection of additional types of abnormalities. Also, the machine learning algorithm performed by the system 10 can include multivariate/multichannel analysis to determine whether a multivariable gradient of sections is stronger than a sum of partial gradients. In further examples, the system 10 can display a 3D view of heart conductance on the display device 12 to visualize the anatomy and/or conduction of the heart as another way to build trust and confidence in the machine learning algorithm performed by the system 10.

In further examples, the interpretation output 202 can include morphology statements when comparing the electrocardiogram waveform 70 with a previous electrocardiogram waveform 72. For example, the interpretation output 202 can include "Compared to the patients previous ECG, the highlighted segment appears to be shorter with a greater slope."

Figure 9:
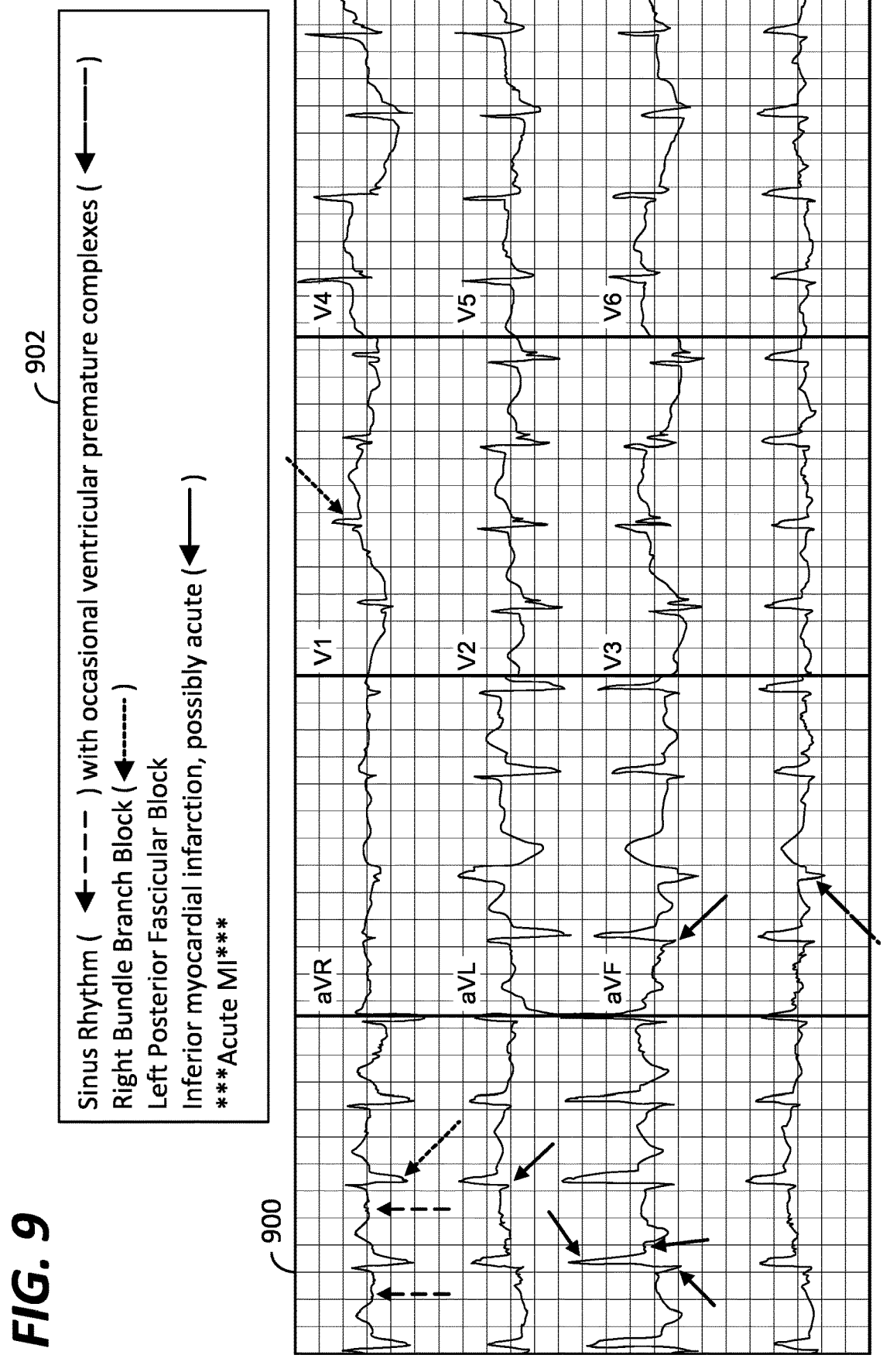
FIG. 9 shows an example of an electrocardiogram waveform that can be displayed on the graphical user interface of FIG. 2, the electrocardiogram waveform having interpretation outputs displayed as arrows indicating the parts of the QRS-T cycle that are abnormal.

FIG. 9 shows an example of an electrocardiogram waveform 900 that can be displayed on the GUI 150 generated by the system 10. The electrocardiogram waveform 900 includes interpretation outputs displayed as arrows indicating the parts of the QRS-T cycle that are abnormal. The arrows can be color-coded and/or have a pattern or other visual indicator to match a corresponding statement in a morphology statement box 902 (e.g., "terminal R wave in V1 and terminal S wave in I are criteria for RBBB", "the Q waves and ST elevation in II, III, and aVF are indicative of an inferior infarction", and the like). A machine learning algorithm detects these abnormal portions of the P-QRS-T cycle and visually indicates these abnormal portions for a human to interpret (e.g., with sample times in the median beat, which can be used by the GUI 150 to highlight regions in all beats matching that morphology on a normal ECG view).

The various embodiments described above are provided by way of illustration only and should not be construed to be limiting in any way. Various modifications can be made to the embodiments described above without departing from the true spirit and scope of the disclosure.

What is claimed is:

1. A system for interpreting an electrocardiogram, the system comprising:
   at least one processing device; and
   a memory device storing instructions which, when executed by the at least one processing device, cause the at least one processing device to:
   receive the electrocardiogram;
   identify a segment of the electrocardiogram having an abnormality using a machine learning algorithm; and
   assign an interpretation output to the segment of the electrocardiogram having the abnormality, the interpretation output describing a morphology of the abnormality, wherein the interpretation output is assigned by:
   applying a range of transformations to the segment;
   feeding the range of transformations through a convolutional neural network;
   determining which transformation in the range of transformations produces a greatest return to normal; and
   generating the interpretation output as a reverse of the transformation that produces the greatest return to normal.

2. The system of claim 1, wherein the interpretation output includes a textual statement.

3. The system of claim 1, wherein the interpretation output includes a morphology marker.

4. The system of claim 1, wherein the instructions, when executed by the at least one processing device, further cause the at least one processing device to:
   compare the electrocardiogram to a normal electrocardiogram model;
   determine deviations from the normal electrocardiogram model; and
   identify the segment of the electrocardiogram having the abnormality by identifying a largest deviation from the normal electrocardiogram model.

5. The system of claim 1, wherein the machine learning algorithm includes saliency mapping.

6. The system of claim 1, wherein the machine learning algorithm includes activation mapping.

7. A system for generating an electrocardiogram, the system including:
   one or more electrodes for receiving heart electrical signals;
   at least one processing device; and
   a memory device storing instructions which, when executed by the at least one processing device, cause the at least one processing device to:
   generate the electrocardiogram based on the heart electrical signals;
   display the electrocardiogram on a display device;
   identify a segment of the electrocardiogram having an abnormality using a machine learning algorithm; and
   assign an interpretation output to the segment of the electrocardiogram having the abnormality, the interpretation output describing a morphology of the abnormality, wherein the interpretation output is assigned by:
   applying a range of transformations to the segment;
   feeding the range of transformations through a convolutional neural network;
   determining which transformation in the range of transformations produces a greatest return to normal; and
   generating the interpretation output as a reverse of the transformation that produces the greatest return to normal.

8. The system of claim 7, wherein the interpretation output includes a textual statement.

9. The system of claim 7, wherein the interpretation output includes a morphology marker.

10. The system of claim 7, wherein the instructions, when executed by the at least one processing device, further cause the at least one processing device to:
   compare the electrocardiogram to a normal electrocardiogram model;
   determine deviations from the normal electrocardiogram model; and
   identify the segment of the electrocardiogram having the abnormality by identifying a deviation from the normal electrocardiogram model.

11. The system of claim 7, wherein the machine learning algorithm includes saliency mapping.

12. The system of claim 7, wherein the machine learning algorithm includes activation mapping.

13. The system of claim 7, further comprising:
   one or more leads, each lead of the one or more leads having a first end for attachment to a chest of a patient, and an opposite second end operatively connected to the at least one processing device.

14. A method of interpreting an electrocardiogram, the method comprising:

generating the electrocardiogram based on heart electrical signals;

displaying the electrocardiogram;

identifying a segment of the electrocardiogram having an abnormality using a machine learning algorithm; and assigning an interpretation output to the segment of the electrocardiogram having the abnormality, the interpretation output describing a morphology of the abnormality, wherein the interpretation output is assigned by:

applying a range of transformations to the segment;

feeding the range of transformations through a convolutional neural network;

determining which transformation in the range of transformations produces a greatest return to normal; and generating the interpretation output as a reverse of the transformation that produces the greatest return to normal.

15. The method of claim 14, further comprising:

comparing the electrocardiogram to a normal electrocardiogram model;

determining deviations from the normal electrocardiogram model; and identifying the segment of the electrocardiogram having the abnormality by identifying a deviation from the normal electrocardiogram model.

16. The method of claim 14, wherein the interpretation output includes a textual statement.

17. The method of claim 14, wherein the machine learning algorithm includes activation mapping.

* * * * *